United States Patent

Marka et al.

[11] Patent Number: 5,934,888
[45] Date of Patent: *Aug. 10, 1999

[54] ASPIRATOR PUMP

[75] Inventors: Rudolf Marka, Darmstadt; Stefan Maier, Weiterstadt; Matthias Peuker, Hanau; Hans-Joachim Kühn, Wiesbaden; Walter Scheller, Maintal, all of Germany

[73] Assignee: Heraeus Med GmbH, Hanau, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/844,298

[22] Filed: Apr. 18, 1997

[30] Foreign Application Priority Data

Apr. 27, 1996 [DE] Germany ............ 196 16 954

[51] Int. Cl.⁶ .................................. F04B 45/02
[52] U.S. Cl. ............ 417/473; 417/480; 417/533; 417/903
[58] Field of Search .............. 417/229, 473, 417/480, 533, 539, 903; 604/74, 75, 153, 182

[56] References Cited

U.S. PATENT DOCUMENTS 2,707,001  4/1955  Hathaway ............ 92/37

FOREIGN PATENT DOCUMENTS 0 271 620 B1  11/1991  European Pat. Off. .
0 245 876 B1   2/1993  European Pat. Off. .
13672          8/1891  United Kingdom ........ 417/473

*Primary Examiner*—Charles G. Freay
*Assistant Examiner*—Cheryl J. Tyler
*Attorney, Agent, or Firm*—Panitch Schwarze Jacobs & Nadel, P.C.

[57] ABSTRACT

An aspirator pump, especially for medical purposes, has a receptacle with two chambers arranged alongside each other, which are connected with a suction tube, and on each of which an element is arranged which is movable approximately parallel to the other, each partially enclosing a hollow space for generating a vacuum. The two movable elements are connected to each other by means of a lever, whose two end parts are attached at the upper area of the respective movable elements, and whose middle part is movably attached in a bearing positioned between the chambers. In the upper area of each movable element a one way valve is installed which opens when the pressure in the hollow space is higher than the surrounding air pressure. An easy operation and cleaning, as well as a reliable aspiration is obtained with the aspirator pump, owing to the fact that at all times a chamber and a movable element enclose a common, variable hollow space, wherein the movable element bounds the upper area of the hollow space. The two hollow spaces are connected through a common manifold with a connection for the suction tube of a catheter, and an additional one way valve is arranged at the entrance of each hollow space into the manifold, which closes when the pressure in the hollow space is greater than the surrounding pressure.

3 Claims, 2 Drawing Sheets

ASPIRATOR PUMP

BACKGROUND OF THE INVENTION

The invention relates to an aspirator pump, especially for medical purposes, having a receptacle with two chambers arranged alongside each other, which are connected with a suction tube, and on each of which an element is arranged which is movable approximately parallel to the other, each partially enclosing a hollow space for generating a vacuum. The two movable elements are connected to each other by means of a lever, whose two end parts are attached at the upper area of the respective movable elements, and whose middle part is movably attached in a bearing positioned between the chambers. In the upper area of each movable element a one way valve is installed, which opens when the pressure in the hollow space is higher than the surrounding air pressure.

An aspirator pump of this type is known, for example, from EP 245 876. With the pump described there, two receptacles are connected with each other through a U-shaped connecting element. Over each container is mounted a vacuum pump, whose movable pump element slides along the sides of the container during the pumping motion. In this way, a vacuum is generated in the space formed by the movable element and the upper end of the receptacle, which through a valve creates a vacuum in the receptacle and thereby sucks secretions or other fluids or vomit from, for example, the mouth of a patient. The two movable pump elements arranged alongside one another are connected with each other through a common lever, so that with every motion of the lever one of the two movable elements creates at all times a vacuum for sucking in through the catheter. In this way, dead times in the operation of the pump are avoided. The pump functions very reliably, but is also relatively expensively constructed. The cleaning of the pump which is necessary following every aspiration requires a very costly disassembly. Both receptacles are openly connected with each other, so that with every stroke motion in a relatively large volume, a vacuum is generated by a relatively small stroke of a movable element each time.

A completely different type of aspirator pump is known from EP 271 620. The hand-operated pump described there has a single hollow space in which a vacuum is generated for evacuating body fluids and the like. The hand operation requires a relatively high mechanical effort, for example owing to the use of return springs. Due to the alternating of suction times and dead times in connection with the operation of this pump, continuous suction is not possible, so that the suction process runs correspondingly slowly. Moreover, owing to the periodic interruption of the suction process, a check valve at the distal end of the catheter is necessary. In addition to this, working with this pump is very tiring over a long period of time, as the work necessary for evacuation is performed exclusively by opening and closing the hand of the operator.

BRIEF SUMMARY OF THE INVENTION

It is an object of the present invention, proceeding from the disadvantages of the described state of the art, to make available an aspirator pump which is easy to operate as well as easy to clean, and which makes possible a reliable aspiration.

This object is accomplished through the invention in that at any given time one chamber of the receptacle and a movable element enclose a variable hollow space, wherein the movable element bounds the upper area of the hollow space, and in that the two hollow areas are connected through a common manifold with a connection for the suction tube, wherein an additional one way valve is arranged at the entrance to each hollow space into the manifold, which closes when the pressure in the hollow space is greater than the surrounding pressure. An aspirator pump of this type can operate with a minimum of component parts, since the entire hollow space can be bounded by a unitary material, wherein the movable element is preferably constructed as a bellows. The container can be simply and thereby economically produced and constructed as a disposable container, so that a cleaning after use is not necessary, as the container can then be eliminated along with its contents. Of course, it is also possible to clean the container, especially when it is made of an autoclavable material. Owing to the fact that both hollow spaces are indeed arranged alongside each other, but have no open connection, and a different pressure can thereby build up in the two hollow spaces, a vacuum is formed at all times only in one of the two adjacent hollow spaces, which is then correspondingly powerful. By alternating creation of an underpressure in the two containers, a continuous aspiration is possible.

The lever can appropriately be constructed as footplate, so that through a back and forth movement of the foot of an operator on the lever, a vacuum is alternatingly formed in the two hollow spaces. In this connection, the lever is suitably fastened detachably to the movable elements in order to facilitate cleaning or to make possible a reuse of the lever when removing the receptacle, which is constructed as a disposable container.

It is appropriate for the receptacle to be anchored in a base housing which has a base plate and side walls, and for the base housing to have a bearing for the lever. In this manner, a particularly high stability for the aspirator pump can be attained.

BRIEF DESCRIPTION OF THE SEVERAL VIEWS OF THE DRAWING

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
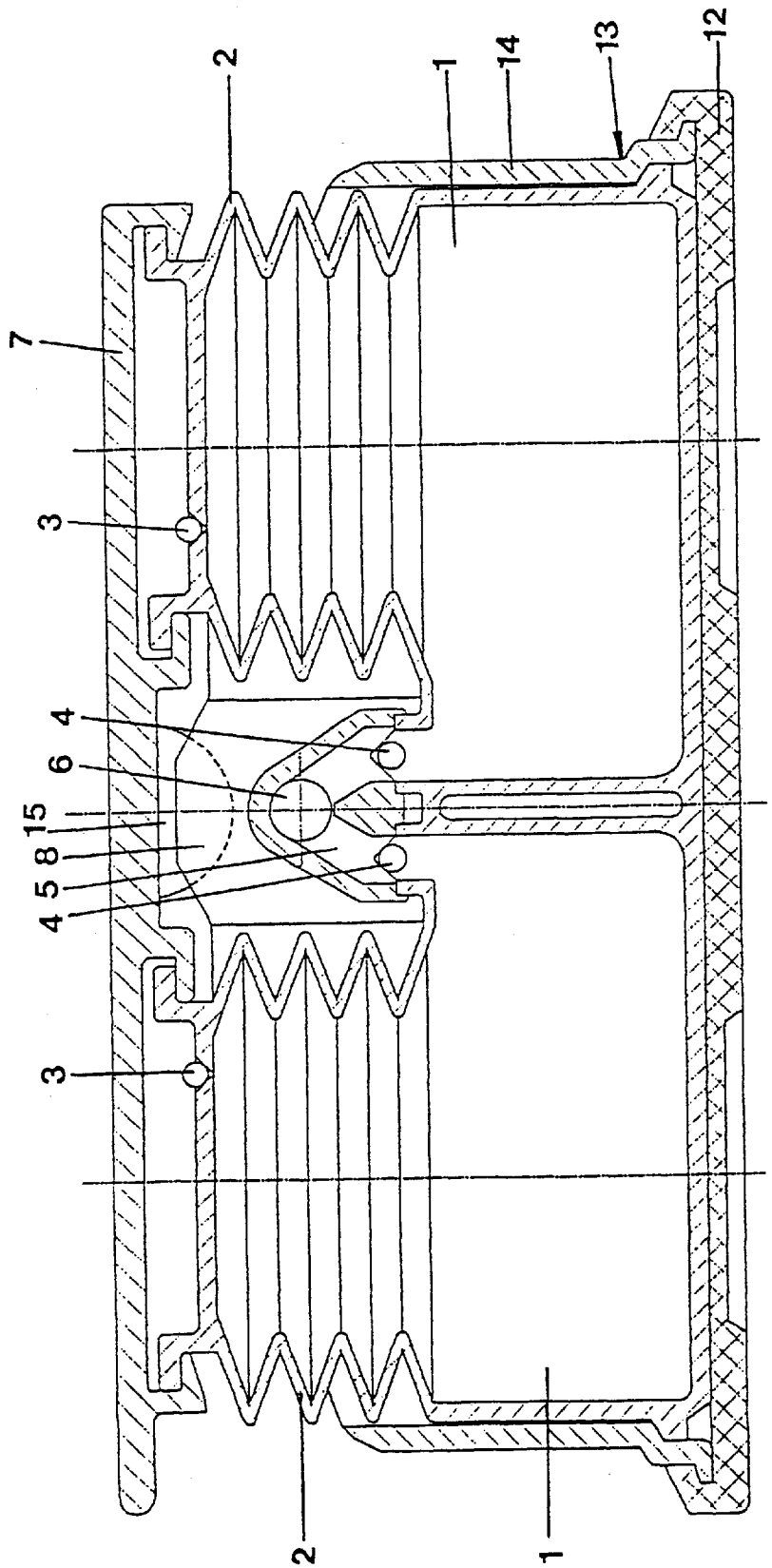
FIG. 1 shows an aspirator pump of the invention in cross section.

The aspirator pump has a receptacle with two chambers 1 arranged alongside each other, whose upper side is bounded by a movable element in each case. The movable element 2 serves to create the vacuum in the common hollow space formed by the receptacle 1 and the movable element 2. On the flat upper side of the movable element 2, which is constructed as a bellows, a one way valve 3 is installed which opens when the bellows is pushed together so that the overpressure in the interior of the hollow space arising from the pushing together is reduced. When the one bellows is pushed down, the second bellows arranged next to it is at the same time drawn apart, so than an underpressure arises in the corresponding hollow space. Through this underpressure, the second one way valve 4 opens, so that a vacuum is formed in the manifold 5 and the suction tube 6 connected thereto, and by means of this, secretions or the like can be evacuated from a body cavity, for example the mouth of an emergency patient.

The lifting or falling motion takes place through the lever 7 which is constructed as a footplate, which is movably fastened with bearing bolt 15 in a bearing 8. On the underside of the lever 7, recesses 9 are arranged in which the lever 7 is slid on corresponding opposing pieces 10 on the upper sides of the movable elements 2. The lever 7 can thereby be very easily detached from the movable elements 2 of the aspirator pump.

Figure 2:
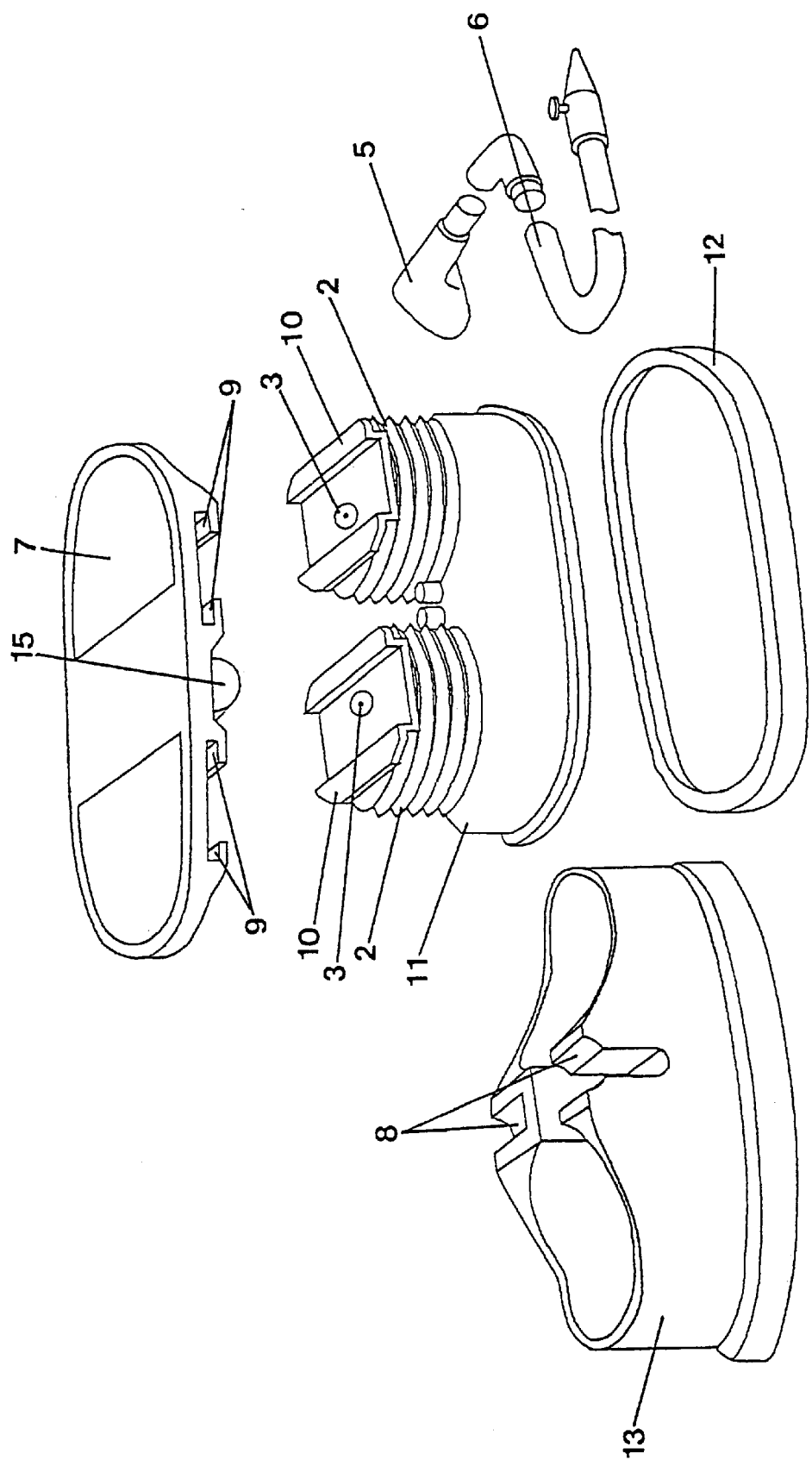
FIG. 2 shows an exploded perspective representation of the aspirator pump of the invention.

The receptacle with the chambers 1 is incorporated into a housing 11 (see FIG. 2). This housing is mounted on a bottom plate 12 in the base housing 13 and thereby achieves a high degree of stability. The connection of the bottom plate 12 and side walls 14 of the base housing 13 with the housing 11 therein can take place by snapping the edges of the individual parts into each other, if these are constructed of a material with sufficient flexibility, as for example an elastic plastic. The lever 7 is at the same time fastened in the bearing 8 arranged in the base housing 13.

An aspirator pump of this type is very easy to assemble. When the common hollow area or the housing 11 with the two hollow spaces is constructed as a disposable container, this unit can easily be removed from the base housing 13 and disposed of, while the base housing 13 and the lever 7 can be easily cleaned and reused.

It will be appreciated by those skilled in the art that changes could be made to the embodiment described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An aspirator pump, especially for medical purposes, comprising:

a one-piece receptacle having a single housing, a lower base, and a divider forming two adjacent hollow chambers; each of said chambers having a movable element connected thereto, and each said movable element including a first one way valve on an upper surface thereof;

a lever having a lower surface with recesses, said recesses detachably receive said upper surface of said movable elements, a middle section intermediate said recesses, said middle section being pivotally mounted on a bearing and being positioned between said adjacent hollow chambers of said receptacle;

a detachable manifold disposed above said divider of said adjacent chambers and below said middle section of said lever, said manifold having a suction tube connected to each of said adjacent chambers and a second pair of one way valves installed beneath said detachable manifold and adjacent said divider whereby each of said first one way valves opens when pressure in the respective hollow chamber is higher than surrounding air pressure and each of said second one way valves closes when pressure in the respective hollow chamber is higher than surrounding air pressure and each of said second one way valves closes when pressure in the respective hollow chamber is greater than surrounding air pressure; and a common base housing in which the receptacle is removably installed, said common base housing including a bottom plate, side walls removably connected to the bottom plate and an upper surface interconnected with the side walls, the upper surface carrying the bearing on which the middle section of the lever is mounted, said receptacle being removable and replaceable as a single unit by disconnecting the bottom plate from the side walls and disconnecting the lever and the manifold.

2. An aspirator pump according to claim 1 wherein the lever is a foot plate.

3. An aspirator pump according to claim 1 wherein said receptacle with said hollow chambers and each said movable element are disposable.

* * * * *